(12) United States Patent
Qi et al.

(10) Patent No.: US 12,085,513 B2
(45) Date of Patent: Sep. 10, 2024

(54) SAMPLE TESTING METHOD AND SAMPLE ANALYZER

(71) Applicant: SHENZHEN MINDRAY BIO-MEDICAL ELECTRONICS CO., LTD., Shenzhen (CN)

(72) Inventors: Huan Qi, Shenzhen (CN); Wei Luo, Shenzhen (CN); Yuan Xing, Shenzhen (CN); Bo Ye, Shenzhen (CN); Yi Ye, Shenzhen (CN); Shan Yu, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 59 days.

(21) Appl. No.: 18/115,627

(22) Filed: Feb. 28, 2023

(65) Prior Publication Data
US 2023/0251205 A1    Aug. 10, 2023

Related U.S. Application Data

(63) Continuation of application No. PCT/CN2020/112480, filed on Aug. 31, 2020.

(51) Int. Cl.
*G01N 21/89*    (2006.01)
*G01N 33/49*    (2006.01)
(Continued)

(52) U.S. Cl.
CPC ......... *G01N 21/8901* (2013.01); *G01N 33/49* (2013.01); *G01N 35/00029* (2013.01);
(Continued)

(58) Field of Classification Search
CPC .... G01N 15/01; G01N 15/0227; G01N 15/10; G01N 15/1012; G01N 2015/1006;
(Continued)

(56) References Cited

U.S. PATENT DOCUMENTS 9,213,177 B2 * 12/2015 Olson .................. G02B 21/002
9,366,630 B2 *  6/2016 Bouzid ................. G02B 13/22
(Continued)

FOREIGN PATENT DOCUMENTS

CN        103163638 A    6/2013
CN        104730702 A    6/2015
(Continued)

*Primary Examiner* — John R Lee
(74) *Attorney, Agent, or Firm* — Kory D. Christensen

(57) ABSTRACT

Embodiments of the present invention relate to a sample image photographing method and a corresponding sample image photographing apparatus. The method comprises: transporting a sample carrier to be tested to an imaging device; determining a focusing surface representation function of said current sample carrier according to a feature of a sample on said current sample carrier, the focusing surface representation function representing a relationship between horizontal position coordinates and a focusing parameter of each point to be photographed in a sample area of said current sample carrier: controlling a horizontal drive component of a driving device such that said current sample carrier moves continuously horizontally relative to the imaging device; and causing said current sample carrier to always satisfy the focusing surface representation function during the continuous horizontal motion, so that the imaging device continuously photographs an area of interest of said current sample carrier during the continuous horizontal motion.

20 Claims, 10 Drawing Sheets

(51) Int. Cl.
*G01N 35/00* (2006.01)
*G01N 21/17* (2006.01)

(52) U.S. Cl.
CPC ................ *G01N 2021/1765* (2013.01); *G01N 2035/00039* (2013.01)

(58) Field of Classification Search
CPC ..... G01N 2021/135; G01N 2021/1765; G01N 2021/177; G01N 2021/1772; G01N 2021/1774; G01N 2021/1776; G01N 2021/8909; G01N 2021/9518; G01N 21/13; G01N 21/17; G01N 21/89; G01N 21/8901; G01N 21/8903; G01N 21/8914; G01N 21/95; G01N 21/9515; G01N 33/48; G01N 33/483; G01N 33/487; G01N 33/49; G01N 35/00; G01N 35/00029; G01N 2035/00039; G01N 35/02; G02B 21/00; G02B 21/0004; G02B 21/002; G02B 21/24; G02B 21/241; G02B 21/244; G02B 21/36; G02B 21/361; G02B 21/362; G02B 21/365; G02B 21/367; H04N 23/661; H04N 23/662; H04N 23/665; H04N 23/667; H04N 23/67; H04N 23/671; H04N 23/672; H04N 23/673; H04N 23/675; H04N 23/676; H04N 23/69; H04N 23/695

See application file for complete search history.

(56) References Cited

U.S. PATENT DOCUMENTS

| | | |
|---|---|---|
| 2002/0090127 A1 | 7/2002 | Wetzel et al. |
| 2004/0105000 A1 | 6/2004 | Yuri |
| 2010/0027856 A1 | 2/2010 | Olson et al. |
| 2015/0185462 A1 | 7/2015 | Inomata et al. |
| 2020/0379232 A1 | 12/2020 | Feirer et al. |
| 2022/0408025 A1* | 12/2022 | Jiang ..................... H04N 23/80 |
| 2023/0251205 A1* | 8/2023 | Qi ......................... G02B 21/367 |

FOREIGN PATENT DOCUMENTS

| | | |
|---|---|---|
| CN | 106990518 A | 7/2017 |
| CN | 109085695 A | 12/2018 |
| CN | 109239900 A | 1/2019 |
| CN | 111399208 A | 7/2020 |
| CN | 111458835 A | 7/2020 |
| JP | 2004191959 A | 7/2004 |
| JP | 2009223164 A | 10/2009 |

* cited by examiner

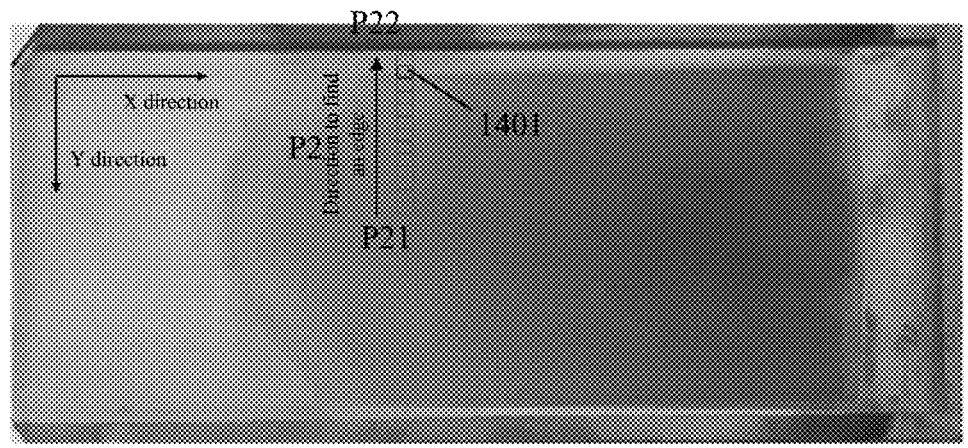
FIG. 14
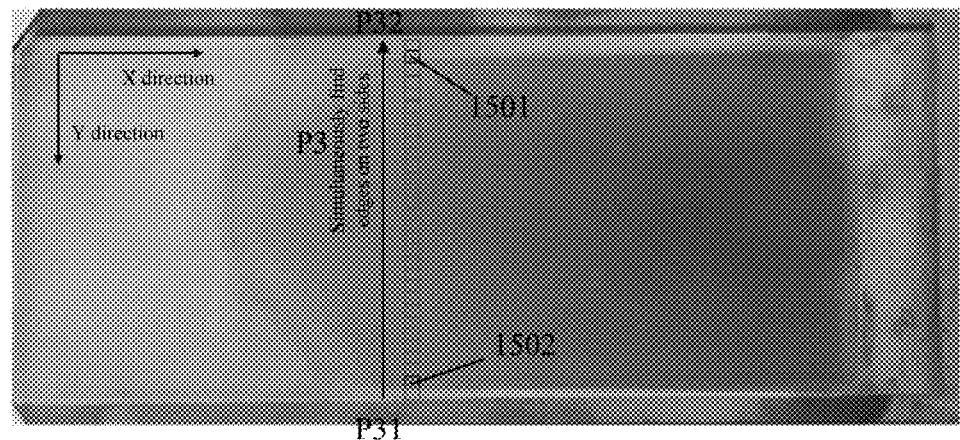
FIG. 15
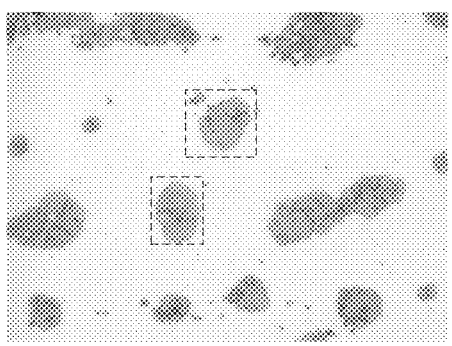      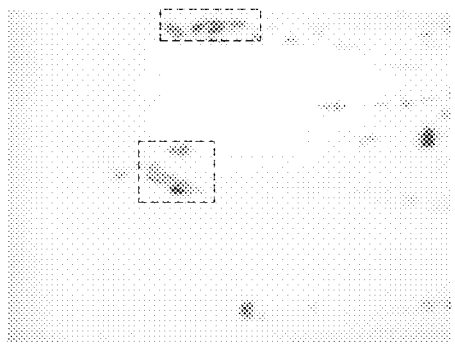
FIG. 16                FIG. 17

SAMPLE TESTING METHOD AND SAMPLE ANALYZER

CROSS-REFERENCE TO RELATED APPLICATIONS

This application is a continuation of International Application No. PCT/CN2020/112480, filed Aug. 31, 2020, for SAMPLE IMAGE PHOTOGRAPHING METHOD AND SAMPLE IMAGE PHOTOGRAPHING APPARATUS, which is incorporated herein by reference in its entirety.

TECHNICAL FIELD

The disclosure relates to the field of sample image photographing, and in particular to a sample image photographing method and a sample image photographing apparatus.

BACKGROUND

A sample image analyzer, for example, a cell morphology analyzer or a urine analyzer, is an apparatus for analyzing cells or formed elements, etc. in a sample such as blood, body fluid, bone marrow; urine, or a tissue. The cell morphology analyzer may also be referred to as a blood cell digital image analyzer or digital microscope, and is configured to analyze cells in a sample such as blood (for example, peripheral blood), body fluid, or bone marrow smeared on a slide.

The blood cell digital image analyzer can automatically load or unload a blood smear, complete cell location and photographing and cell recognition and pre-classification, and present a photographed blood cell image to a user, and can replace the work of artificial microscopy to some extent. Compared with artificial microscopy, the blood cell digital image analyzer has a greatly increased test speed.

The current blood cell digital image analyzer perform photographing by: an electric motor firstly driving a blood smear to move relative to an imaging device to allow a first target position on the blood smear to appear within the field of view of the imaging device, and then the electric motor stopping and the imaging device focusing on and photographs a sample at the first target position to obtain a clear image of the first target position: next, the electric motor driving the blood smear to move relative to the imaging device again to allow a next target position on the blood smear to appear within the field of view of the imaging device, and then the electric motor stopping again and the imaging device focusing on and photographing the sample at the next target position to obtain a clear image of the next target position; and repeating the above steps. In this way, the electric motor starts and stops repeatedly, and the imaging device needs to perform focusing and photographing for each field of view, resulting in a low speed. In the case of large area to be photographed or more fields of view to be photographed, the photographing time is greatly prolonged, which greatly influences the overall detection efficiency of the cell morphology analyzer.

SUMMARY

In order to solve, at least in part, the above technical problems, a task of the disclosure is to provide an improved solution which can be implemented, within a predetermined photographing time, to enable an imaging device to continuously photograph a test sample while a driving device enables the test sample to continuously move relative to the imaging device, so that the driving device does not need to stop driving for focusing of the imaging device, thereby greatly increasing the photographing speed and also prolonging the service life of the driving device.

To fulfill the task of the disclosure, a first aspect of the disclosure relates to a sample image photographing method, including:

transporting a test sample carrier by means of a sample carrier transport device to an imaging device including a camera and an objective lens;

obtaining horizontal position coordinates of at least three reference points in a sample area of the test sample carrier by means of a control device;

moving the test sample carrier horizontally relative to the imaging device by means of a horizontal drive component of a driving device to allow the at least three reference points to separately stop within a field of view of the imaging device, so that the imaging device separately focuses on the at least three reference points;

determining a focusing surface representation function of the test sample carrier by means of the control device according to the horizontal position coordinates and focusing parameters of the at least three reference points, the focusing surface representation function representing a relationship between horizontal position coordinates and the focusing parameter of each point to be photographed in the sample area of the test sample carrier;

continuously moving the test sample carrier horizontally relative to the imaging device by means of the horizontal drive component of the driving device;

causing the test sample carrier to always satisfy the focusing surface representation function during the continuous horizontal movement by means of at least one of a vertical drive component of the driving device and the imaging device; and continuously photographing a sample in an area of interest of the test sample carrier by means of the imaging device during the continuous horizontal movement to obtain sample images.

A second aspect of the disclosure relates to a sample image photographing method, including:

transporting a test sample carrier to an imaging device;

determining a focusing surface representation function of the current test sample carrier according to a feature of a sample on the current test sample carrier, the focusing surface representation function representing a relationship between horizontal position coordinates and the focusing parameter of each point to be photographed in a sample area of the current test sample carrier;

controlling a horizontal drive component of a driving device to continuously move the current test sample carrier horizontally relative to the imaging device; and causing the current test sample carrier to always satisfy the focusing surface representation function during the continuous horizontal movement, so that the imaging device continuously photographs an area of interest of the current test sample carrier during the continuous horizontal movement.

A third aspect of the disclosure relates to a sample image photographing apparatus, including:

an imaging device, which is provided with a camera and an objective lens and is configured to photograph an image of a sample on a sample carrier;

a sample carrier holding device configured to hold the sample carrier;

a driving device, which is provided with a horizontal drive component configured to enable the sample carrier held by the sample carrier holding device to move horizontally relative to the imaging device and a vertical drive component configured to enable the sample carrier held by the sample carrier holding device to move vertically relative to the imaging device; and a control device, which is in communication connection with the driving device and the imaging device and is configured to obtain horizontal position coordinates of at least three reference points in a sample area of a test sample carrier held by the sample carrier holding device, control the horizontal drive component to move the test sample carrier horizontally relative to the imaging device to allow the at least three reference points to separately stop within a field of view of the objective lens of the imaging device, and control the imaging device to focus on the at least three reference points to obtain focusing parameters of the at least three reference points, determine a focusing surface representation function of the test sample carrier according to the horizontal position coordinates and the focusing parameters of the at least three reference points, the focusing surface representation function representing a relationship between horizontal position coordinates and the focusing parameter of each point to be photographed in the sample area of the test sample carrier, control the horizontal drive component to continuously move the test sample carrier horizontally relative to the imaging device, control at least one of the vertical drive component and the imaging device to cause the test sample carrier to always satisfy the focusing surface representation function during the continuous horizontal movement, and control the imaging device to continuously photograph a sample in an area of interest of the test sample carrier during the continuous horizontal movement to obtain sample images.

A fourth aspect of the disclosure relates to a sample image photographing apparatus, including:

an imaging device, which is provided with a camera and an objective lens and is configured to photograph an image of a sample on a sample carrier;

a sample carrier holding device configured to hold the sample carrier;

a driving device, which is provided with a horizontal drive component configured to enable the sample carrier held by the sample carrier holding device to move horizontally relative to the imaging device and a vertical drive component configured to enable the sample carrier held by the sample carrier holding device to move vertically relative to the imaging device; and a control device, which is in communication connection with the driving device and the imaging device and is configured to determine, according to a feature of a sample on the current test sample carrier, a focusing surface representation function of the current test sample carrier held by the sample carrier holding device, the focusing surface representation function representing a relationship between horizontal position coordinates and the focusing parameter of each point to be photographed in a sample area of the current test sample carrier, control the horizontal drive component to continuously move the current test sample carrier horizontally relative to the imaging device, control at least one of the vertical drive component and the imaging device to cause the current test sample carrier to always satisfy the focusing surface representation function during the continuous horizontal movement, and control the imaging device to continuously photograph a sample in an area of interest of the current test sample carrier during the continuous horizontal movement to obtain sample images.

In the technical solutions proposed in the aspects of the disclosure, before a new test sample is photographed every time, a preset focusing function related to a feature of the test sample formed on a carrier of the test sample is established; and then during a formal photographing process, the driving device continuously moves the test sample relative to the imaging device, while the driving device or the imaging device causes the test sample to always satisfy the preset focusing function during the continuous movement relative to the imaging device, and the imaging device photographs at the same time. In this way, the driving device does not need to be started and stopped repeatedly, and the imaging device does not need to focus on each field of view, thereby greatly increasing the sample photographing speed.

BRIEF DESCRIPTION OF THE DRAWINGS

FIGS. 13 to 15 are schematic diagrams of determining a target position of an edge of a blood film by means of a method provided according to an embodiment of the disclosure:

FIGS. 16 and 17 are cell images of a tail area of a blood smear provided according to an embodiment of the disclosure:

DETAILED DESCRIPTION

The technical solutions in the embodiments of the disclosure will be described below clearly and completely in conjunction with the accompanying drawings in the embodiments of the disclosure. The embodiments described are merely some rather than all of the embodiments of the disclosure. Based on the embodiments in the disclosure, all other embodiments that would have been obtained by those of ordinary skill in the art without any creative effort shall fall within the scope of protection of the disclosure.

As already described at the beginning, a sample image analyzer is configured to analyze cells or formed elements, etc. in a sample such as blood, body fluid, bone marrow; urine, or a tissue. The sample image analyzer, for example, a cell image analyzer, is configured to photograph a cell image of a sample on a blood smear and present the cell image to a user for analysis by the user. The sample image analyzer may also be a urine analyzer for analyzing urine components in a counting cell.

In an embodiment, a sample carrier is a slide. In this embodiment, the sample may be, for example, peripheral blood, which forms a blood film on a slide, and a photographed object includes erythrocytes, leukocytes, blood platelets, etc. in the peripheral blood. The sample may also be, for example, bone marrow; which forms a bone marrow smear on a slide. The bone marrow examination generally includes examination on cells of various mature stages, such as erythrocyte series, granulocyte series, lymphocyte series, monocyte series and plasmacytic series, and other cells such as megakaryocytes, reticular cells, phagocytes, endothelial cells and fat cells. For another example, the sample may be other excretions and secretions, which form a sample smear on a slide, and the photographed object includes, for example, cell components in a sample such as faces, vaginal secretion, seminal fluid, a prostatic fluid or sputum, commonly erythrocytes, leukocytes, crystals, pathogenic microorganisms, epithelial cells, parasites, sperms, trichomonad, choline bodies of prostate, granular cells of prostate, alveolar macrophages, and tumor cells. Alternatively, the sample may be body cavity fluid, which forms a body cavity fluid smear on a slide, and the photographed object includes cerebrospinal fluid, serous cavity effusion, joint cavity effusion, and cell components in amniotic fluid, commonly erythrocytes, leukocytes, leukocyte clusters, bacteria, yeast-like fungi, epithelial cells, parasites, etc. Alternatively, the sample may also be exfoliated cells, which form a sample smear on a slide, and the photographed object includes epithelial cells, mesothelial cells, cancer cells, erythrocytes, leukocytes, macrophages or tissue cells, a necrotic material (mucus, bacterial aggregate, fungal aggregate, plant cells, cotton fibers, dye residues, etc.), parasite, etc.

Figure 1:
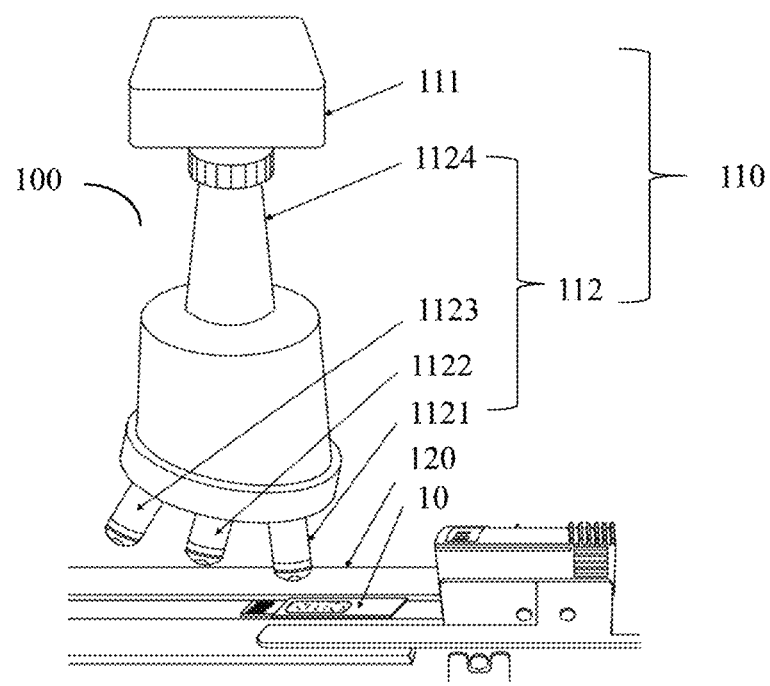
FIG. 1 is a schematic structural diagram of a cell image analyzer.

In another embodiment, the sample carrier is a counting cell, the sample is urine which forms urine sediment in the counting cell, and the photographed object is urine formed elements, mainly including erythrocytes, leukocytes, leukocyte clusters, bacteria, yeast-like fungi, epithelial cells, small round epithelial cells, crystals, hyaline casts, non-hyaline casts, mucous filaments, etc. commonly found in urine. FIG. 1 shows a schematic structural diagram of main components of an existing cell image analyzer 100. The cell image analyzer 100 includes at least an imaging device 110 and a smear moving device 120. The imaging device 110 includes a camera 111 and a lens group 112 and is configured to photograph cells in a sample smeared on a smear 10. The smear moving device 120 is configured to move the smear 10 relative to the imaging device 110, so that the imaging device 110 photographs a cell image of a specific area of the smear 10. The lens group 112 may include a first objective lens 1121 and a second objective lens 1122. The first objective lens may be, for example, a 10× objective lens, and the second objective lens may be, for example, a 40× objective lens or a 100× objective lens. The lens group 112 may further include a third objective lens 1123 and/or an adapter tube 1124. Certainly, the lens group 112 may also include only a 40× objective lens or a 100× objective lens.

Figure 2:
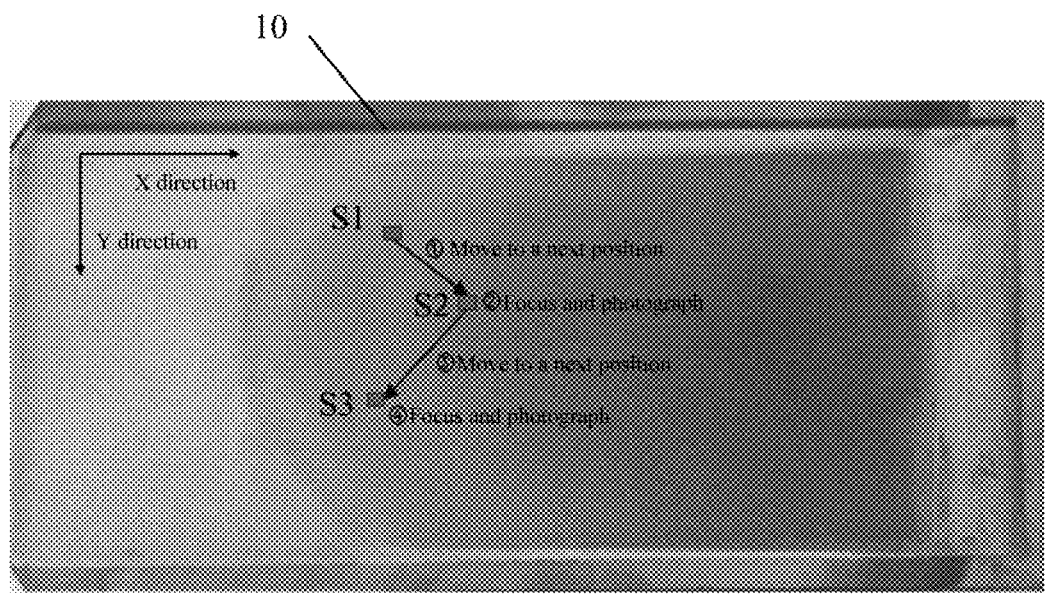
FIG. 2 is a schematic flowchart of a focusing photographing mode of an existing cell image analyzer.

At present, a photographing mode of the cell image analyzer is generally shown in FIG. 2. A horizontal electric motor firstly drives a blood smear 10 to move horizontally relative to an imaging device, i.e., to move in an X direction and/or a Y direction, to enable a first target position S1 on the blood smear 10 to be within a field of view of the imaging device, and then the horizontal electric motor stops driving, while a vertical electric motor drives the blood smear to move vertically relative to the imaging device (in a Z direction perpendicular to the XY plane), so as to focus on and photograph a sample at the first target position S1 to obtain a clear image of the first target position S1. Next, the vertical electric motor stops moving, and the horizontal electric motor drives the blood smear to move horizontally relative to the imaging device again to allow a next target position S2 on the blood smear 10 to be within the field of view of the imaging device; and then the horizontal electric motor stops again, and the vertical electric motor drives the blood smear to move vertically relative to the imaging device, so that the imaging device focuses on and photographs the sample at the next target position S2 to obtain a clear image of the next target position S2. Then the above steps are repeated to photograph a clear image of a next target position S3, and the steps are repeated until images of all preset target positions are photographed. In this case, the horizontal electric motor and the vertical electric motor starts and stops repeatedly, and the imaging device needs to perform focusing and photographing for each field of view; resulting in a low photographing speed.

In addition, in the field of pathological slices, standard slicing is generally used to establish a predicted focusing surface of the whole slice. Then, for all the test slices, the same predicted focusing surface is used to scan the test slices. However, this solution can only be applied to pathological slices, because they are prepared in such a way that each test slice is even, so that the systematic focusing surface can be predicted using the standard slice.

For blood smears, they are prepared in a relatively complicated manner. Blood smears are usually prepared by a smear preparation device that may be used for preparation of smears of samples such as blood and body fluid. The smear preparation device includes a sampling mechanism for drawing a sample, a slide loading mechanism for moving a slide to an operating line, a sample adding mechanism for adding the sample onto the slide, a slide making mechanism for smearing the sample on the slide, and a drying mechanism for drying a blood film on the slide. A sampling device (for example, a sampling needle) in the sampling mechanism is firstly used for sample aspiration. When the sampling is completed, the sample adding mechanism is ready to drip blood onto the slide. Accordingly, the slide loading mechanism takes the slide and loads the slide to a corresponding position to facilitate the blood dripping operation. A blood dripping needle of the sample adding mechanism drips the sample onto the slide, and then a slide making operation is performed, so that the blood on the slide is smeared into a blood film by the slide making mechanism. In general, after the slide making operation is completed, the blood film on the slide may be dried to stabilize the morphology of the blood film. The blood smears prepared in this way have non-uniform thickness (for example, gradually thinning from a head to a tail in a smearing direction), and prepared blood smears are different in shape and thickness due to different characteristics of the blood samples. The blood smears have deviations in focusing surface even if they are prepared by a same smear preparation device, much less the blood smears prepared by different smear preparation devices or the blood smears prepared artificially.

Therefore, in order to quickly scan and photograph samples, the disclosure proposes a sample image photographing method and a sample image photographing apparatus to firstly predict a focusing surface of part or all of a sample area and then photograph while moving in an area of interest, which ensures that the area of interest is in a clearly focused state in each photographing, and finally the photographing of the whole area of interest is completed. That is to say, a driving device does not need to stop for focusing, that is, the driving device continuously drives a test sample to move relative to the imaging device during a predetermined photographing time, while the imaging device continuously photographs the test sample at predetermined photographing intervals. Therefore, by means of this method, neither the horizontal electric motor nor the vertical electric motor needs to be started and stopped repeatedly, and the imaging device does not need to focus on each field of view, thereby greatly improving the photographing efficiency.

The technical solution proposed by the disclosure can be advantageously applied to full-slide scanning and photographing for leukocytes and platelet aggregation on a blood smear under a 100× objective lens, or scanning and photographing for only platelet aggregation and abnormal leukocytes at an edge and a tail of a blood film on a blood smear.

Certainly, the technical solution proposed by the disclosure can also be used to scan and photograph other user-specified areas, or can be used to scan and photograph a body fluid sample. This is not specifically limited herein.

Figure 3:
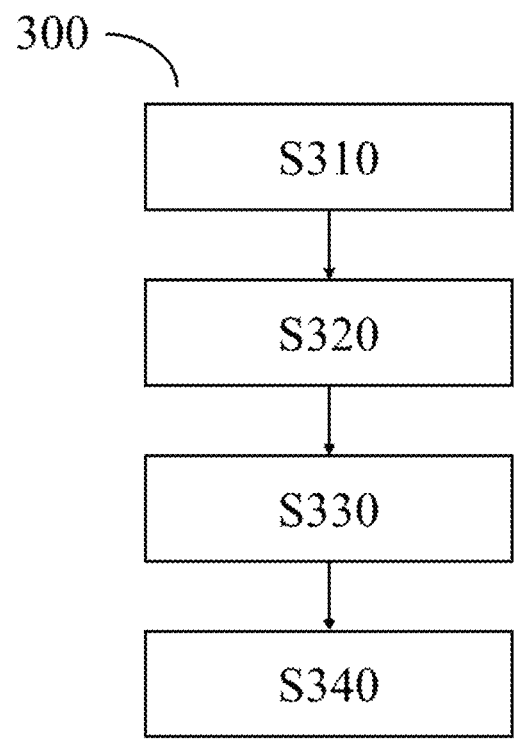
FIG. 3 is a schematic flowchart of a sample image photographing method provided according to an embodiment of the disclosure.

As shown in FIG. 3, an embodiment of the disclosure firstly proposes a sample image photographing method 300, including the steps S310 to S340 as follows.

At step S310, a test sample carrier is firstly transported to an imaging device, for example, a sample carrier transport device automatically transports the test sample carrier to an objective lens, such as a 100× objective lens, of the imaging device.

In the embodiment of the disclosure, the test sample carrier is a carrier that carries a test sample. The carrier may be a slide, and accordingly, the test sample may be blood or bone marrow or body fluid. The carrier may also be a counting cell, and accordingly, the test sample may be urine. In a preferred embodiment, the test sample carrier is a test slide smeared with a blood sample.

At step S320, a focusing surface representation function of the current test sample carrier is determined according to a feature of a sample on the current test sample carrier (i.e., a test sample carrier currently located under the objective lens), this focusing surface representation function representing a relationship between horizontal position coordinates and the focusing parameter of each point to be photographed in a sample area of the current test sample carrier.

In this step, for each newly loaded test sample carrier, before formal photographing, a new focusing function f (S, P) is firstly established according to the feature of the test sample carrier itself, where S represents horizontal position coordinates (X, Y) of a point to be photographed, and P represents the focusing parameter of the point to be photographed. Here, the horizontal position coordinates represent a relative position relationship between the test sample carrier and the imaging device in a horizontal plane, and the focusing parameter may be a focusing distance (focusing height) or a parameter of the camera of the imaging device.

In addition, it should be noted that the feature of the sample on the current test sample carrier may include the feature of the sample itself, such as parameter results of a blood routine test of the sample, and may also include features such as the appearance and thickness of the sample formed on the sample carrier.

In some embodiments, several reference points may be selected from the sample area of the current test sample carrier to predict focusing parameters of all points to be photographed. That is, step S320 may include: obtaining horizontal position coordinates (X, Y) of at least three reference points in the sample area of the current test sample carrier and focusing parameters of the at least three reference points under the imaging device; and establishing the focusing surface representation function of the current test sample carrier according to the horizontal position coordinates and the focusing parameters of the at least three reference points.

In some embodiments, determining the focusing surface representation function of the test sample carrier according to the horizontal position coordinates and the focusing parameters of the at least three reference points includes: solving a plane equation $a*X+b*Y+c*Z+d=0$ according to the horizontal position coordinates and the focusing height of the at least three reference points to obtain a predicted focusing surface, where X and Y represent the horizontal position coordinates, Z represents the focusing height, and a, b, c and d represent coefficients to be solved of the plane equation.

In some embodiments, the number of the at least three reference points is greater than 10.

Figure 4:
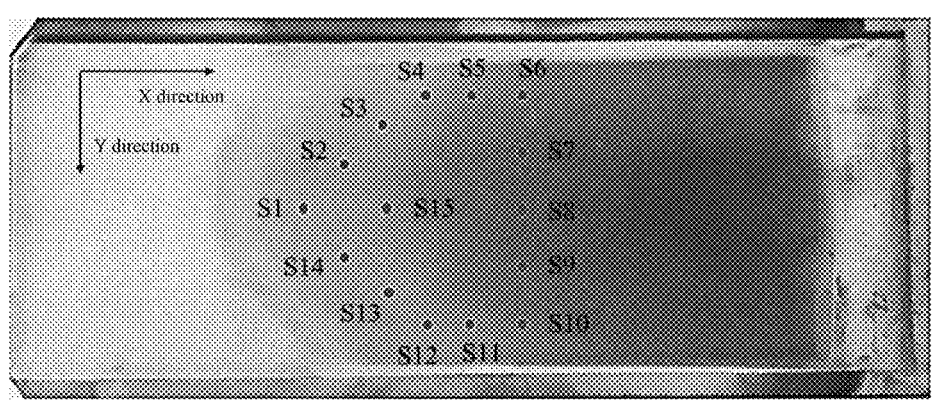
FIG. 4 is a schematic diagram of obtaining reference points in a sample image photographing method provided according to an embodiment of the disclosure.
Figure 5:
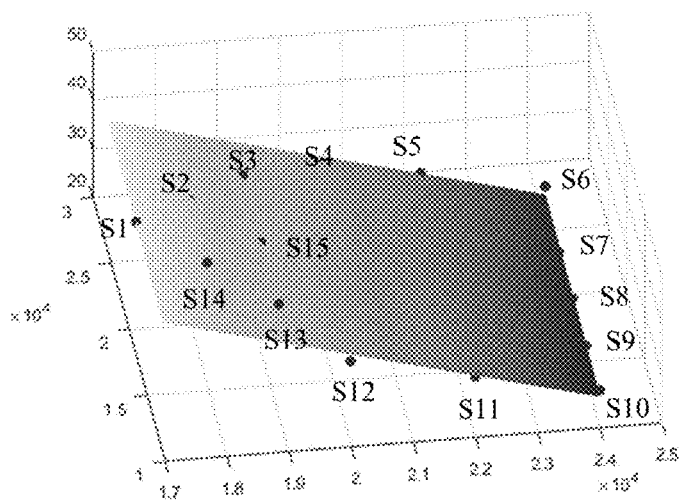
FIG. 5 is a schematic diagram of a focusing surface provided according to an embodiment of the disclosure.

Taking a blood smear as a test sample carrier as an example, as shown in FIG. 4, a plurality of reference points, such as 15 reference points S1 to S15, are first selected from a blood sample area of the blood smear, where positions (horizontal position coordinates) of the reference points are settable. The blood smear then moves horizontally relative to the imaging device to allow the 15 reference points to separately stop within the field of view of the imaging device, so that the imaging device separately focuses on the 15 reference points and records the focusing position or focusing height (focusing distance) of each reference point. A focusing surface of the whole blood smear is then fitted according to the horizontal position coordinates and the focusing positions of the 15 points, as shown in FIG. 5, so as to predict the focusing position of any place of the whole blood smear.

It should be understood that the predicted focusing surface may also be a fitted surface.

At step S330, a horizontal drive component of a driving device is controlled to continuously move the current test sample carrier horizontally relative to the imaging device.

In some embodiments, the horizontal drive component includes a first electric motor, such as an X-direction electric motor, and a second electric motor, such as a Y-direction electric motor, and this step includes: continuously moving the test sample carrier horizontally relative to the imaging device by means of at least one of the first electric motor and the second electric motor. For example, at step S330, the first electric motor or the second electric motor may drive the test sample carrier to move horizontally relative to the imaging device, or the first electric motor and the second electric motor may simultaneously drive the test sample carrier to move horizontally relative to the imaging device.

At step S340, the current test sample carrier always satisfies the focusing surface representation function during the continuous horizontal movement, so that the imaging device continuously photographs an area of interest of the current test sample carrier during the continuous movement.

In this way, during the continuous movement, the driving device does not need to stop for focusing, and since the current test sample carrier always satisfies the focusing surface representation function during the continuous horizontal movement, i.e., the current test sample carrier is in a focused state, the imaging device can dynamically scan and photograph a clear image of each point to be photographed in the sample area of the test sample carrier.

In some preferred embodiments, the focusing parameter is a focusing height, i.e., a distance between a lens of the imaging device and the test sample carrier, and a representation form of the focusing surface representation function includes a predicted focusing surface. In this case, step S340 includes: controlling a vertical drive component of the driving device to move the current test sample carrier vertically relative to the imaging device, so that the current test sample carrier is always on the predicted focusing surface during the continuous horizontal movement.

Further, the vertical drive component of the driving device is controlled to move the current test sample carrier vertically relative to the imaging device while the horizontal drive component of the driving device is controlled to continuously move the current test sample carrier horizontally relative to the imaging device, so that the current test sample carrier is always on the predicted focusing surface during the continuous horizontal movement. That is to say, as the horizontal drive component continuously moves the current test sample carrier horizontally relative to the imaging device, the vertical drive component moves the current test sample carrier vertically relative to the imaging device to allow the current test sample carrier to be always in a focused state, so that the imaging device can dynamically scan and photograph a clear image of each point to be photographed of the test sample carrier.

In some embodiments, the vertical drive component of the driving device moves the current test sample carrier vertically relative to the imaging device, which may be implemented in such a way that the imaging device is fixed (the height of the lens is unchanged), while the vertical drive component of the driving device drives the current test sample carrier to move vertically, so that the current test sample carrier is always on the focusing surface: or the current test sample carrier is fixed, while the vertical drive component of the driving device drives the imaging device (lens) to move vertically, so that the current test sample carrier is always on the focusing surface.

In some alternative or additional implementations, the focusing parameter includes an imaging parameter or a camera parameter of the imaging device. In this case, step S340 includes: adjusting the parameter of the imaging device, so that the current test sample carrier always satisfies the focusing surface representation function during the continuous horizontal movement. For example, the height of the current test sample carrier relative to the lens of the imaging device is unchanged, and the current test sample carrier is always in a focused state by means of adjusting the camera parameter. In a specific example, the camera parameter of the imaging device is adjusted to implement zooming (to implement focusing when the relative height is unchanged), and optical zoom may be generally used, that is, zooming is implemented by means of moving a lens in a zoom lens group in a microscope or camera, and includes internal zooming and external zooming. During internal zooming, the lens does not zoom (the length of the lens or the height of the objective lens is unchanged). Certainly, the current test sample carrier is allowed to be always in a focused state by means of both the driving of the vertical drive component and the adjustment of the camera parameter.

Figure 6:
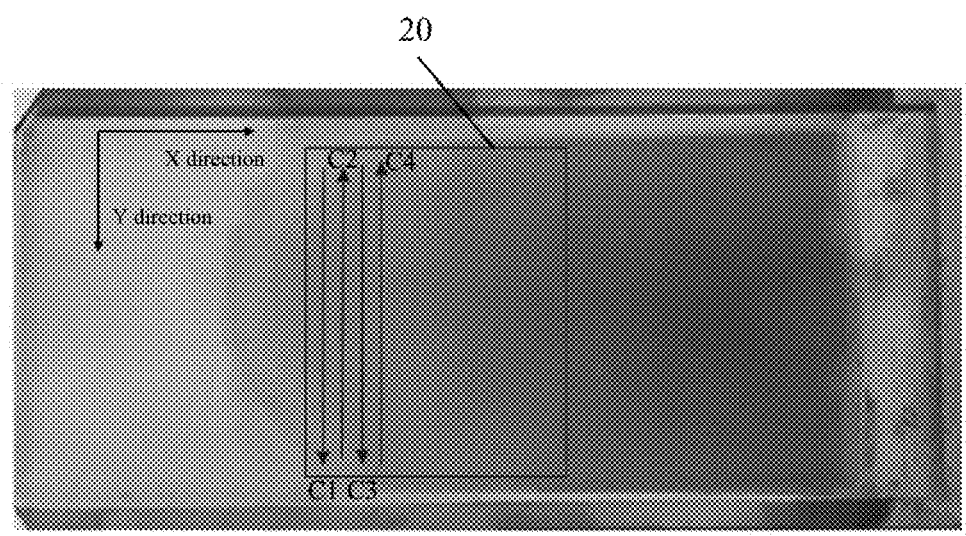
FIGS. 6 and 7 are schematic diagrams of scanning an area of interest in a sample image photographing method provided according to an embodiment of the disclosure.
Figure 7:
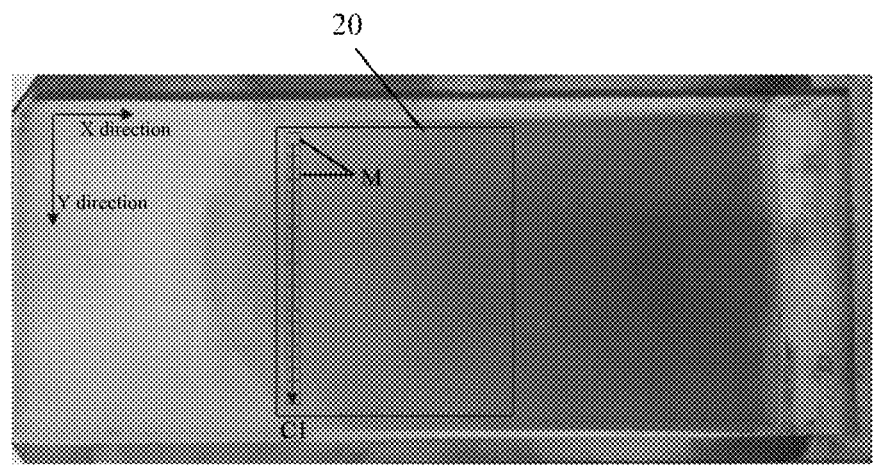

In a specific example, taking a blood smear as an example, the driving device includes a first electric motor as an X-direction electric motor, a second electric motor as a Y-direction electric motor, and a third electric motor as a Z-direction electric motor. The imaging device is fixed, the first electric motor drives the blood smear to move in an X direction, the second electric motor drives the blood smear to move in a Y direction, and the third electric motor drives the blood smear to move in a Z direction, that is, the first electric motor and the second electric motor drive the blood smear to move horizontally relative to the imaging device, while the third electric motor drives the blood smear to move vertically relative to the imaging device, that is, to move in a direction perpendicular to the horizontal plane, so as to adjust the focusing height. In this example, the movement scanning of an area of interest is shown in FIGS. 6 and 7. For example, the area of interest 20 may be scanned and photographed column-by-column from C1 to C4, and certainly, may also be scanned and photographed row-by-row or in an inclined mode. The column-by-column scanning and photographing mode is shown in FIG. 6. The Y-direction electric motor drives a test blood smear to move along the column C1 relative to the imaging device, and the imaging device photographs a sample image on the column C1 of the blood smear. The X-direction electric motor then drives the test blood smear to move to the column C2 relative to the imaging device, the Y-direction electric motor drives the test blood smear to move along the column C2 relative to the imaging device, and the imaging device photographs a sample image on the column C2 of the blood smear. The steps are repeated to the column C4. The scanning and photographing process of each column is shown in FIG. 7. The Y-direction electric motor drives the test blood smear to move, relative to the imaging device, directly from one end of C1 to the other end of C1 at a constant speed, and the Z-direction electric motor (the vertical drive component) drives the test blood smear to move vertically relative to the imaging device in the Z direction (perpendicular to the XY plane or a plane where the blood smear is horizontally placed) to ensure that the test blood smear is always in a focused state. During this period, the camera of the imaging device continuously photographs to obtain images M of the area of a whole column (each small box in the figure represents one image). During the X/Y-direction electric motor moving the test blood smear to the target position, while the Z-direction electric motor also moves the test blood smear to a predicted focusing surface at a target position, that is, the X/Y electric motor and the Z electric motor move and stop simultaneously, so as to ensure that the test blood smear is always on the focusing surface during the movement.

In some embodiments, in order to further ensure that the imaging device can photograph a clear image during the continuous movement of the test sample carrier relative to the imaging device, the exposure time of the camera of the imaging device should match the speed of movement of the horizontal drive component, that is, the exposure time is less than or equal to the distance by which the test sample carrier is moved horizontally relative to the imaging device within the exposure time/the speed of movement of the horizontal drive component. In order to prevent image blurring, the horizontally moving distance should be set relatively small. That is, a driving speed of the horizontal drive component is designed in such a way that the distance by which the test sample carrier is moved horizontally relative to the imaging device within the exposure time of the imaging device is not greater than 2 micrometers, especially not greater than 1 micrometer, especially in the case of using a 40× or 100× objective lens.

In some embodiments, the method of the focusing surface representation function according to the disclosure can be used to photograph large-area sample images in a short time. For example, during the continuous horizontal movement, the area photographed by the imaging device per second is not less than 1 square millimeter, especially not less than 1.3 square millimeters, especially in the case of using a 40× or 100× objective lens. For example, the imaging device continuously photographs sample images in an area of at least 20 square millimeters of the test sample carrier during a continuous horizontal movement of at most 15 seconds.

In some preferred embodiments, the at least three reference points are selected from the area of interest. In the case of only photographing the area of interest on the blood smear, it is advantageous to select reference points from the area of interest.

It should be understood that the selected reference points may be evenly distributed in the area of interest or located in a circumscribed circle of the area of interest. In addition, the reference points may be selected automatically according to a preset rule, or may be selected manually.

Further, the at least three reference points are not in a same straight line. Alternatively or additionally, the at least three reference points are respectively selected from different areas of interest. For example, when it is necessary to photograph three areas of interest, the at least three reference points are respectively selected from the three areas of interest.

Figure 8:
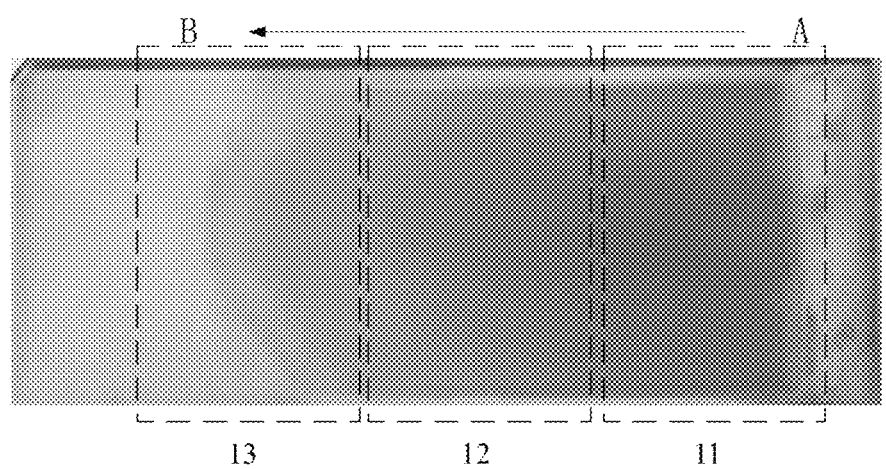
FIGS. 8 and 9 are schematic diagrams of distribution of portions of a blood film of a blood smear provided according to an embodiment of the disclosure.
Figure 9:
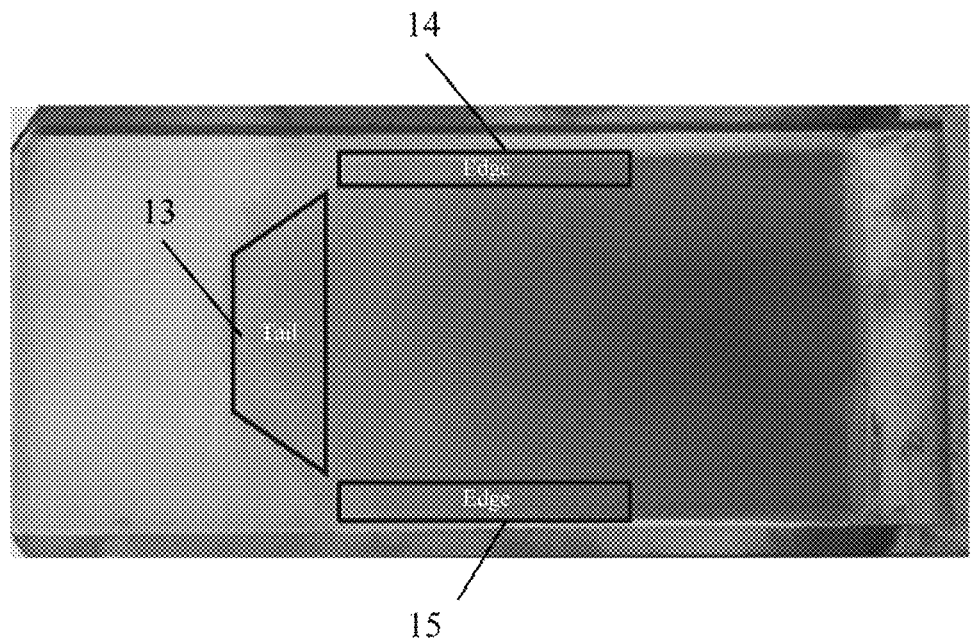

In a preferred embodiment, the test sample carrier is a test slide 10 smeared with a blood sample, and the blood sample forms a blood film on the slide. As shown in FIG. 8, the blood film includes a head 11, a body 12 and a tail 13 on the test slide in a smearing direction (an arrow direction from A to B). As shown in FIG. 9, the area of interest includes at least one of a tail 13 and edges 14 and 15 of a blood film. Preferably, the area of interest includes the tail 13, the upper edge 14 and the lower edge 15 of the blood film. In this case, the at least three reference points may be respectively selected from the tail 13, the upper edge 14, and the lower edge 15.

It should be understood that the area of interest may also include all sample areas of the test sample carrier, that is, all sample areas of the test sample carrier are comprehensively scanned and photographed.

Due to the difference in shape of blood films smeared on different blood smears, the position of the area of interest such as the tail and the edges also changes. Therefore, in general, only an approximate position of the area of interest can be known in advance. If the position of the area of interest is fixedly preset on the blood smear, the area of interest may not be completely photographed, or even no image of the area of interest can be photographed, resulting in the lack of important information of the blood smear, which may cause a doctor to be unable to make an accurate clinical judgment. Therefore, the method of photographing while moving according to the embodiment of the disclosure may be used to quickly locate the position of the area of interest on the blood smear and photograph an image in the area of interest as completely as possible.

Therefore, in some embodiments, step S330 includes: continuously moving the test sample carrier horizontally relative to the imaging device according to a predetermined photographing path by means of the horizontal drive component of the driving device, the predetermined photographing path passing through the area of interest. Accordingly, step S340 includes: continuously photographing a plurality of sample images of the test sample carrier along the predetermined photographing path by means of the imaging device during the continuous horizontal movement. The method 300 further includes step S350: determining a target position of the area of interest according to the plurality of sample images, that is, a target position of the area of interest on the test sample carrier. For example, a predetermined photographing path is predetermined by means of a possible position of the area of interest, so that the predetermined photographing path passes through the area of interest, and an accurate position of the area of interest is obtained by means of analyzing sample images in the predetermined photographing path.

Further, in the case where the test sample carrier is a test blood smear, step S350 includes: sequentially analyzing image features of at least two successively photographed sample images in the plurality of sample images; and determining that the photographing position of one of the at least two sample images is the target position of the area of interest, if the change of the image features of the at least two successively photographed sample images satisfies a preset condition. The image feature includes, for example, a cell area. In this case, the cell area in the analyzed sample image is recognized according to the difference in grayscale or color of the cells and the background in the analyzed sample image. If the change in area of cell areas of the at least two successively photographed sample images satisfies a preset condition, the photographing position of the first or last photographed sample image in the at least two sample images is the target position of the area of interest.

Figure 10:
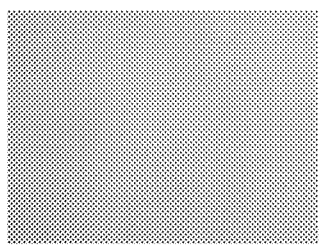
FIGS. 10 to 12 are cell images of different areas of a blood smear provided according to an embodiment of the disclosure.
Figure 11:
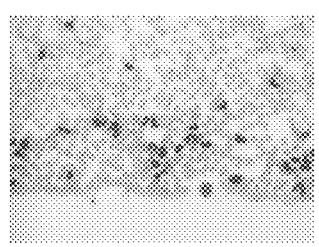
Figure 12:
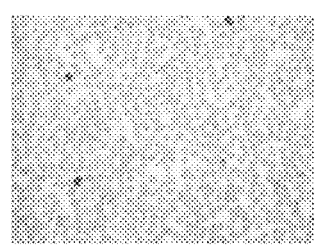

For example, when the area of interest includes the upper edge 14 and/or the lower edge 15 of the blood film, if the image feature of the first or last photographed sample image of the at least two successively photographed sample images indicates that the cell image corresponds to a partially blank cell area (as shown in FIG. 10), and the image features of the remaining sample images indicate that the remaining sample images correspond to a completely blank area (as shown in FIG. 11) or a whole cell area (as shown in FIG. 12), the photographing position of the first or last photographed sample image is the target position of the edge.

Figure 13:
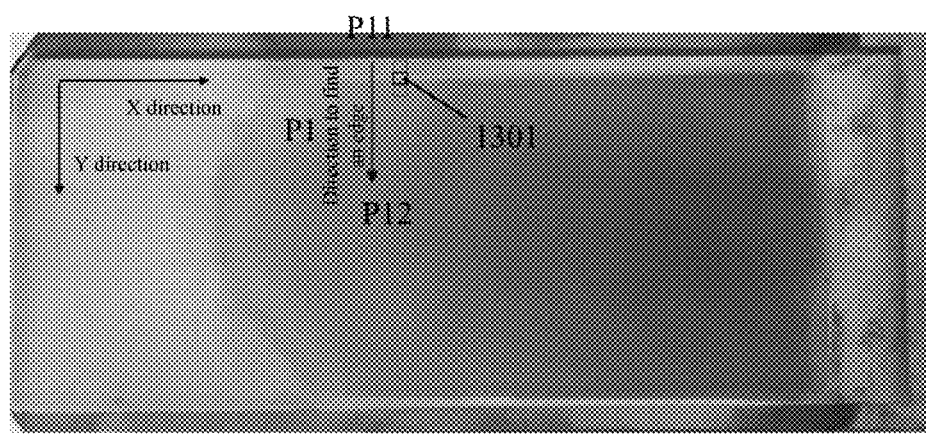

As shown in FIG. 13, the upper edge 14 may be found from blank positions on two sides to the middle, that is, an initial position P11 of a photographing path P1 is set at the blank positions on two sides of the blood film, and a final position P12 is set at the body 12 of the blood film. The method of photographing while moving according to the embodiment of the disclosure is used to photograph a plurality of images (each small box is an image) along the photographing path perpendicular to the edge of the blood smear (as shown in the arrow direction in the figure), firstly passing through the completely blank area, then passing through the edge area with a blank and cells, and then completely entering the cell area. The actual distance from a photographing start point to an edge position is determined according to the initial photographing position, the image position (a specific image) of the edge area and a spacing distance between adjacent images, and then the actual position of the upper edge 14 is determined. In FIG. 13, the position of an image 1301 may be considered as the actual position of the upper edge 14.

In another example, as shown in FIG. 14, the upper edge 14 may also be found from a middle position to blank positions on two sides, that is, an initial position P21 of a photographing path P2 is set at the body 12 of the blood film, and a final position P22 is set at the blank positions on two sides of the blood film. The method of photographing while moving according to the embodiment of the disclosure is used to photograph a series of images along the photographing path perpendicular to the edge of the blood smear (as shown in the arrow direction in the figure), firstly passing through the area completely with cells, then passing through the edge area with a blank and cells, and then completely entering the blank area. The actual distance from a photographing start point to an edge position is determined according to the initial photographing position, the image position (a specific image) of the edge area and a spacing distance between adjacent images, and then the actual position of the upper edge 14 is determined. In FIG. 14, the position of an image 1401 may be considered as the actual position of the upper edge 14.

In still another example, the area of interest includes edges of two long sides of the blood film, that is, an upper edge 14 and a lower edge 15. Here, photographing may be directly performed from a blank position on one side to a blank position on the other side, as shown in FIG. 15, that is, an initial position P31 and a final position P32 of a photographing path P3 are both set in blank areas on two sides of the blood film. The method of photographing while moving in the embodiment of the disclosure is used to photograph a series of images along the photographing path perpendicular to the edge of the blood smear (as shown in the arrow direction in FIG. 15), and then be located to edge positions on two sides. The actual distance from a photographing start point to an edge position is determined according to the image position (a specific image) of the edge area and a spacing distance between adjacent images, and then the actual position of the edge is determined. In FIG. 15, the position of an image 1501 may be considered as the actual position of the upper edge 14, and the position of an image 1502 may be considered as the actual position of the lower edge 15.

In some other embodiments, the area of interest includes a tail of the blood film, and step 350 includes: determining that the photographing position of the first or last photographed sample image in the at least two sample images is a first target position of the tail, if the change of the image features of the at least two successively photographed sample images indicates that the tail feature of aggregation of erythrocytes into clusters and/or a small cell area appears.

FIGS. 16 and 17 are schematic diagrams of a tail of a blood film according to an embodiment of the disclosure, FIG. 16 being the schematic diagram of the tail relatively close to a body of a blood film, and FIG. 17 being the schematic diagram of a tail edge close to a blank area. In the tail area, the cells, especially erythrocytes, aggregate into clusters and/or there is a small cell area. Dashed boxes in FIGS. 16 and 17 mark clusters formed by cell aggregation. By means of the features of the tail, it is possible to determine whether the current photographing position is at the tail by means of analyzing the features of the image.

Figure 18:
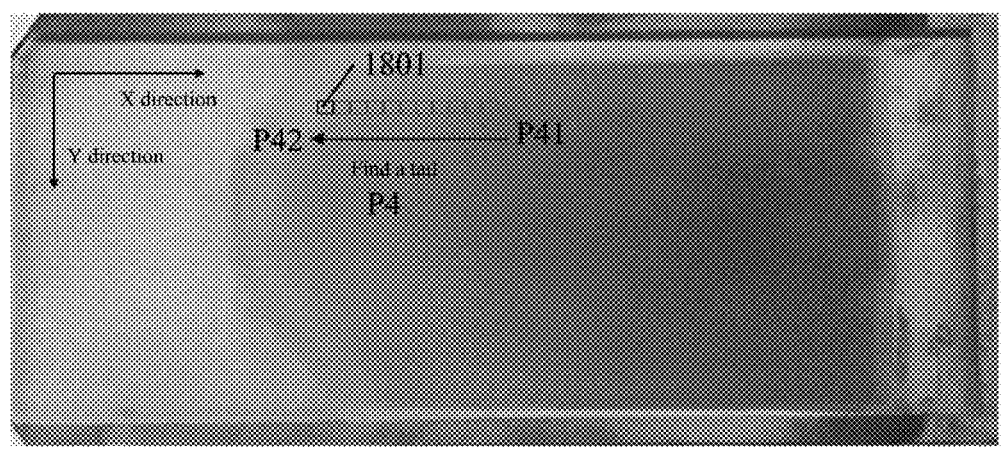
FIGS. 18 and 19 are schematic diagrams of determining a target position of a tail of a blood film by means of a method provided according to an embodiment of the disclosure.

In an example, as shown in FIG. 18, a plurality of cell images may be photographed from the body to the tail along a photographing path P4 (as indicated by the arrow direction in FIG. 18) parallel to the edge of the blood smear (an initial position P41 of the photographing path P4 is set at the body 12 of the blood film, while a final position P42 is set at the tail 13 of the blood film) until the tail area where there are small number of cells and a lot of blanks and erythrocytes aggregate into clusters. The actual distance from a photographing start point to a tail position is determined according to the image position (a specific image) of the tail area and a spacing distance between adjacent images, and then the actual position of the tail edge is determined. In addition, since the tail edge is usually arc-shaped, multiple rows of photographing paths in the arrow direction may be chosen to photograph cell images to determine multiple positions of the tail edge, so that the tail area can be subsequently photographed more completely. A start point and an end point of each row of photographing path may be preset and stored. In FIG. 18, the position of an image 1801 may be considered as the position of the tail.

Figure 19:
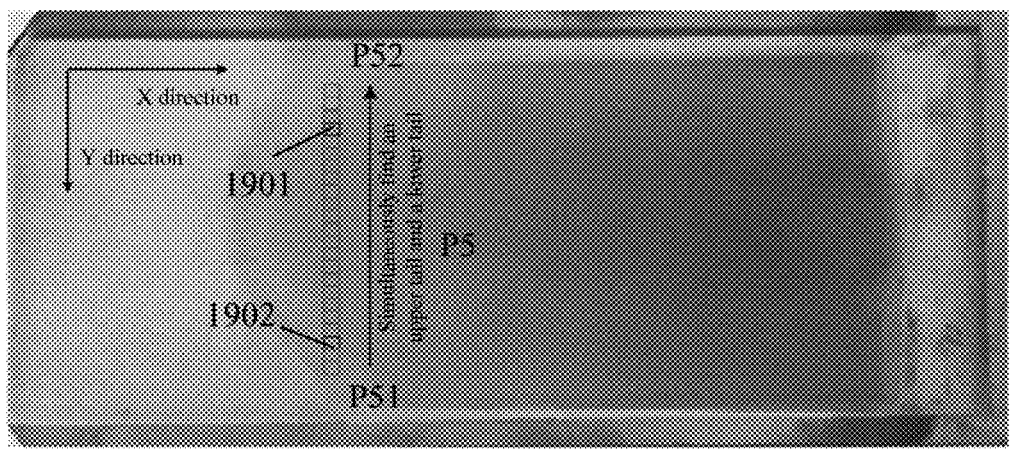

In another example, as shown in FIG. 19, a plurality of cell images may also be photographed from one side to the other side of a photographing path P5 (as indicated by the arrow direction in FIG. 19) perpendicular to the edge of the blood smear (an initial position P51 and a final position P52 of the photographing path P5 are both set in blank areas on two sides of the tail of the blood film), and image positions of an upper tail edge and a lower tail edge are found from the cell images. The actual distance from a photographing start point to a tail position is determined according to the image position (a specific image) of the tail area and a spacing distance between adjacent images, and then the actual position of the tail edge is determined. Similarly, since the tail edge is usually arc-shaped, multiple columns of photographing paths in the arrow direction may be chosen to photograph cell images to determine multiple positions of the tail edge, so that the tail area can be subsequently photographed more completely. A start point and an end point of each column of photographing path may be preset and stored: or a start point and an end point of a first column of photographing path may be preset and stored, and a start point and an end point of a next photographing path may be then determined according to the previous detected tail edge position. In FIG. 19, positions of images 1901 and 1902 may be considered as positions of an upper edge and a lower edge of the tail.

Further, after the target position of the area of interest is determined, it is possible to determine a target photographing path of the area of interest according to the target position of the area of interest, that is, to determine how to photograph the area of interest according to the target position of the area of interest.

For more details about the photographing and location of the area of interest, reference may be made to the patent application, METHOD FOR LOCATING AREA OF INTEREST OF BLOOD FILM ON BLOOD SMEAR AND CELL IMAGE ANALYZER, filed on the same day by the applicant, which is incorporated herein by reference in its entirety.

Figure 20:
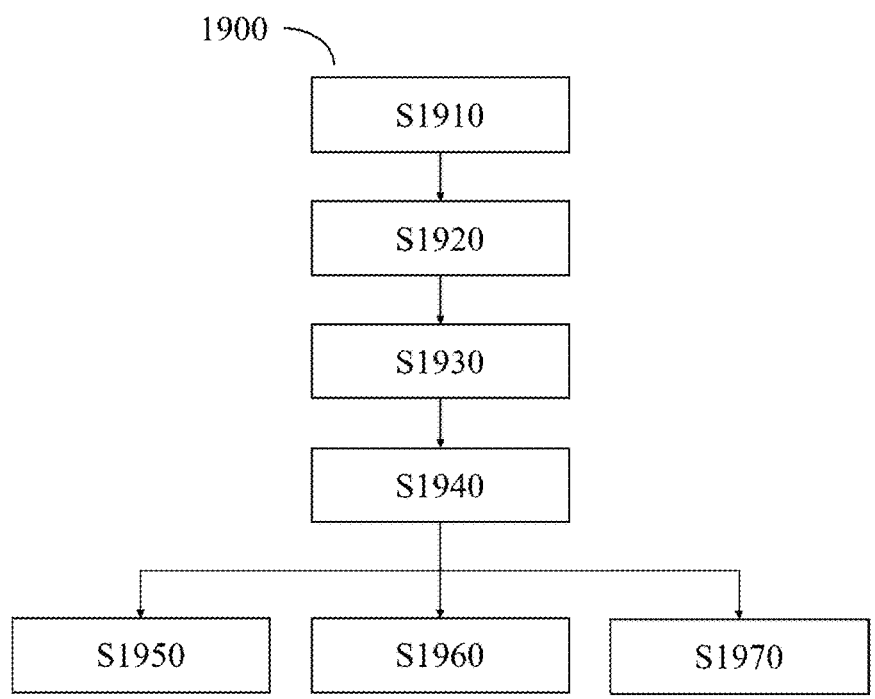
FIG. 20 is a schematic flowchart of another sample image photographing method provided according to an embodiment of the disclosure.

An embodiment of the disclosure further provides another sample image photographing method 1900. As shown in FIG. 20, the sample image photographing method 1900 includes the following steps.

At step S1910, a test sample carrier is transported by a sample carrier transport device to an imaging device including a camera and an objective lens.

At step S1920, horizontal position coordinates of at least three reference points in a sample area of the test sample carrier are obtained by a control device.

At step S1930, the teste sample carrier is moved horizontally relative to the imaging device by a horizontal drive component of a driving device to allow the at least three reference points to separately stop within a field of view of the imaging device, so that the imaging device separately focuses on the at least three reference points.

At step S1940, a focusing surface representation function of the test sample carrier is determined by means of the control device according to the horizontal position coordinates and focusing parameters of the at least three reference points, the focusing surface representation function representing a relationship between horizontal position coordinates and the focusing parameter of each point to be photographed in the sample area of the test sample carrier.

At step S1950, the test sample carrier is continuously moved horizontally relative to the imaging device by the horizontal drive component of the driving device:

At step S1960, the test sample carrier is caused to always satisfy the focusing surface representation function during the continuous horizontal movement by means of at least one of a vertical drive component of the driving device and the imaging device (the vertical drive component and/or the imaging device).

At step S1970, a sample in an area of interest of the test sample carrier is continuously photographed by means of the imaging device during the continuous horizontal movement to obtain sample images.

Steps S1950, S1960, and S1970 are performed synchronously.

It should be noted here that although "horizontal position coordinates" and "horizontal movement" are described here and "vertical movement" is described below; that is, the photographing direction of the imaging device is a vertical direction, the disclosure is not limited thereto. That is, the photographing direction of the imaging device may also be a horizontal direction, the sample carrier continuously performs relative movement in a vertical plane relative to the imaging device, and the focusing distance of the sample carrier relative to the imaging device is a horizontal distance. In other words, the sample carrier continuously perform relative movement relative to the imaging device in a plane direction perpendicular to the photographing direction of the imaging device, and the focusing distance of the sample carrier relative to the imaging device is the distance of the sample carrier relative to the imaging device in the photographing direction of the imaging device.

In an embodiment, the focusing parameter includes a focusing height, and a representation form of the focusing surface representation function includes a predicted focusing surface. Step S1960 includes: moving the test sample carrier vertically relative to the imaging device by means of the vertical drive component of the driving device, so that the test sample carrier is always on the predicted focusing surface during the continuous horizontal movement.

Further, the vertical drive component of the driving device moves the test sample carrier vertically relative to the imaging device while the horizontal drive component of the driving device continuously moves the test sample carrier horizontally relative to the imaging device, so that the test sample carrier is always on the predicted focusing surface during the continuous horizontal movement.

In another alternative or additional embodiment, the focusing parameter includes an imaging parameter of the imaging device. Step S1960 includes: adjusting the parameter of the imaging device by means of the control device, so that the test sample carrier always satisfies the focusing surface representation function during the continuous horizontal movement.

In some embodiments, step S1910 includes: placing the test sample carrier on a testing platform located under the imaging device by means of the sample carrier transport device, that is, fixedly placing the test sample carrier on the testing platform. Accordingly, step S1950 includes: driving the testing platform by means of the horizontal drive component of the driving device to enable the test sample carrier to continuously move horizontally relative to the imaging device. Further, the focusing parameter includes a focusing height, and a representation form of the focusing surface representation function includes a predicted focusing surface. Step S1960 includes: driving the testing platform by means of the vertical drive component of the driving device to enable the test sample carrier to move vertically relative to the imaging device, so that the test sample carrier is always on the predicted focusing surface during the continuous horizontal movement. Preferably, the imaging device is fixed during the continuous horizontal movement, the horizontal drive component drives the testing platform to enable the test sample carrier carried on the testing platform to continuously move horizontally, and the vertical drive component drives the testing platform to enable the test sample carrier carried on the testing platform to move vertically, so that the test sample carrier is always in a focused state during the continuous horizontal movement.

In an alternative embodiment, step S1950 includes: driving the test sample carrier transport device by means of the driving device to enable the test sample carrier to continuously move horizontally relative to the imaging device. Further, Step S1960 includes: driving the test sample carrier transport device by means of the driving device to enable the test sample carrier to move vertically relative to the imaging device, so that the test sample carrier is always on the predicted focusing surface during the continuous horizontal movement. Preferably, the imaging device is fixed during the continuous horizontal movement, the horizontal drive component of the driving device drives the test sample carrier transport device to enable the test sample carrier to move horizontally, and the vertical drive component of the driving device drives the test sample carrier transport device to enable the test sample carrier to move vertically, so that the test sample carrier is always in a focused state during the continuous horizontal movement.

For other advantages and features of the sample image photographing method 1900 provided according to the embodiment of the disclosure, reference may be made to the above description of the sample image photographing method 300 provided according to the embodiment of the disclosure and the embodiment thereof, and details are not described herein again.

Figure 21:
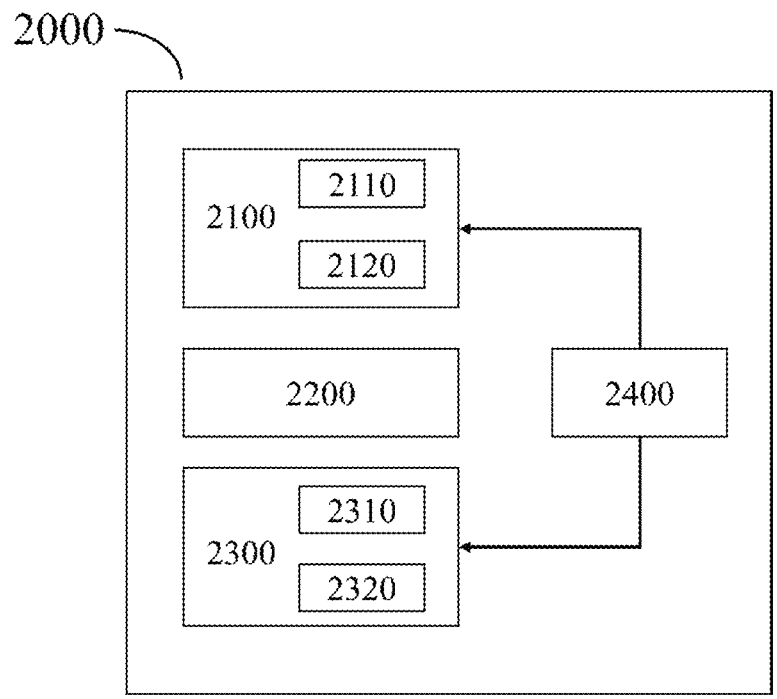
FIG. 21 is a schematic block diagram of a sample image photographing apparatus provided according to an embodiment of the disclosure.

An embodiment of the disclosure further provides a sample image photographing apparatus 2000. As shown in FIG. 21, the sample image photographing apparatus 2000 includes an imaging device 2100, a sample carrier holding device 2200, a driving device 2300, and a control device 2400.

The imaging device 2100 is provided with a camera 2110 and an objective lens 2120 and is configured to photograph an image of a sample on a sample carrier. For a specific example of the imaging device 2100, reference may be made to FIG. 1. The camera 2110 is, for example, a digital camera CCD.

The sample carrier holding device 2200 is configured to hold the sample carrier.

The driving device 2300 is provided with a horizontal drive component 2310 configured to enable the sample carrier held by the sample carrier holding device 2200 to move horizontally relative to the imaging device 2100 and a vertical drive component 2320 configured to enable the sample carrier held by the sample carrier holding device 2200 to move vertically relative to the imaging device 2100.

The control device 2400 is in communication connection with the driving device 2300 and the imaging device 2100 and is configured to
- determine, according to a feature of a sample on the current test sample carrier, a focusing surface representation function of the current test sample carrier held by the sample carrier holding device 2200, the focusing surface representation function representing a relationship between horizontal position coordinates and the focusing parameter of each point to be photographed in a sample area of the current test sample carrier,
- control the horizontal drive component 2310 to continuously move the current test sample carrier horizontally relative to the imaging device 2100,
- control at least one of the vertical drive component 2320 and the imaging device 2100 to cause the current test sample carrier to always satisfy the focusing surface representation function during the continuous horizontal movement, and
- control the imaging device 2100 to continuously photograph a sample in an area of interest of the current test sample carrier during the continuous horizontal movement to obtain sample images.

In an embodiment, the control device 2400 is further configured to determine the focusing surface representation function of the current test sample carrier in the following manner including:
- obtaining horizontal position coordinates of at least three reference points in the sample area of the current test sample carrier and focusing parameters of the at least three reference points under the imaging device; and
- establishing the focusing surface representation function of the current test sample carrier according to the horizontal position coordinates and the focusing parameters of the at least three reference points.

Further, the control device 2400 is further configured to obtain the focusing parameters of the at least three reference points in the following manner including: controlling the horizontal drive component 2310 to move the current test sample carrier horizontally relative to the imaging device 2100 to allow the at least three reference points to stop within a field of view of the objective lens 2120 of the imaging device 2100, and control the imaging device 2100 to focus on the at least three reference points to obtain the focusing parameters of the at least three reference points. That is to say, before the formal photographing of the test sample carrier, the focusing parameters of a plurality of reference points may be obtained in a conventional photographing manner of repeatedly starting and stopping an electric motor, so as to establish a focusing surface representation function.

In a preferred embodiment, the focusing parameter is a focusing height, and a representation form of the focusing surface representation function includes a predicted focusing surface. In this case, in order to cause the test sample carrier to be always in a focused state during the continuous horizontal movement, the control device 2400 is configured to control the vertical drive component 2320 to move the test sample carrier vertically relative to the imaging device 2100, so that the test sample carrier is always on the predicted focusing surface during the continuous horizontal movement. Further, the control device 2400 controls the vertical drive component 2320 to move the test sample carrier vertically relative to the imaging device 2100 while controlling the horizontal drive component 2310 to continuously move the test sample carrier horizontally relative to the imaging device 2100, so that the test sample carrier is always on the predicted focusing surface during the continuous horizontal movement. That is to say, during the formal photographing of the test sample carrier, the control device 2400 controls the horizontal drive component 2310 and the vertical drive component 2320 to move the test sample carrier horizontally and vertically relative to the imaging device 2100.

Figure 22:
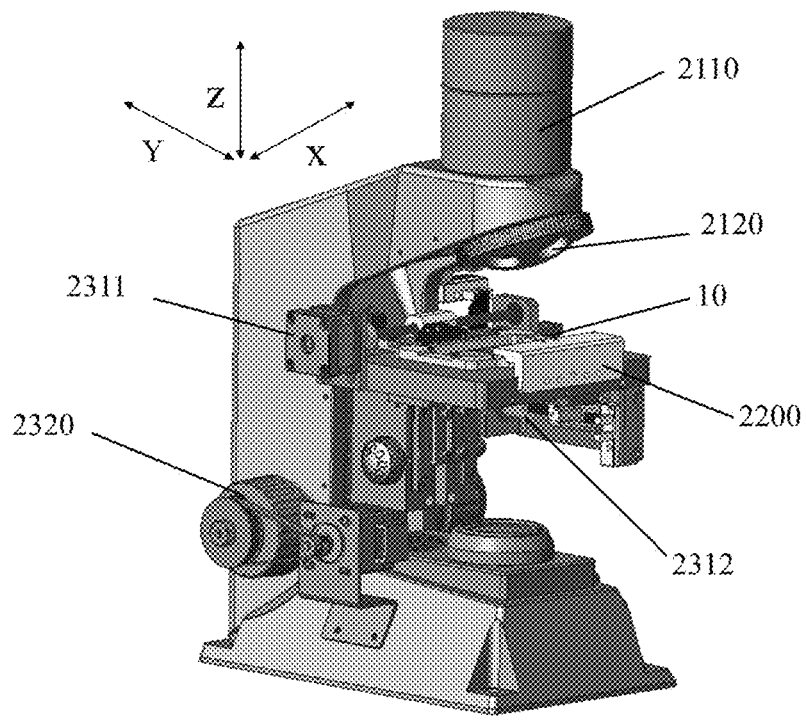
FIG. 22 is a schematic structural diagram of a sample image photographing apparatus provided according to an embodiment of the disclosure.

In an example, as shown in FIG. 22, the horizontal drive component 2310 includes a first electric motor 2311 and a second electric motor 2312, the first electric motor 2311 being configured to enable the test sample carrier 10 to move relative to the imaging device 2100 in a first horizontal direction X, and the second electric motor 2312 being configured to enable the test sample carrier 10 relative to the imaging device 2100 in a second horizontal direction Y perpendicular to the first horizontal direction X. In this case, the control device is further configured to control at least one of the first electric motor and the second electric motor to continuously move the test sample carrier 10 horizontally relative to the imaging device 2100. Further, the vertical drive component 2320 is a third electric motor configured to enable the test sample carrier 10 to move relative to the imaging device 2100 in the vertical direction Z perpendicular to the horizontal plane XY.

In an alternative or additional embodiment, the focusing parameter includes an imaging parameter or a camera parameter of the imaging device. In this case, the control device 2400 is configured to adjust the imaging parameter of the imaging device, so that the test sample carrier always satisfies the focusing surface representation function during the continuous horizontal movement.

In order to prevent image blurring in the case of photographing while moving, the driving speed of the horizontal drive component 2310 (the first electric motor and the second electric motor) is designed such that the distance by which the test sample carrier is moved horizontally relative to the imaging device is not greater than 2 micrometers within the exposure time of the imaging device 2100, especially not greater than 1 micrometer, especially in the case of using a 40× or 100× objective lens, preferably in the case of using a 100× objective lens.

Figure 23:
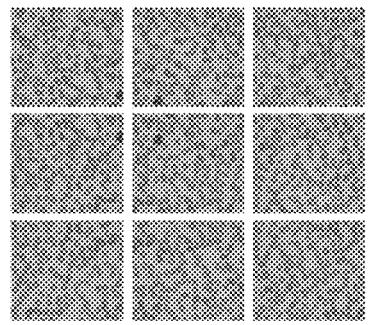
FIGS. 23 and 24 are schematic diagrams of sample images provided according to an embodiment of the disclosure before and after splicing.
Figure 24:
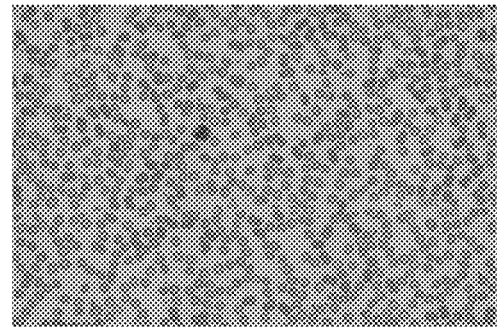

In some embodiments, the driving speed of the horizontal drive component 2310 (the first electric motor and the second electric motor) is determined according to at least one of the predetermined distance of field of view between two successively photographed adjacent images and the photographing frame rate of the imaging device 2100. For example, the electric motor speed is equal to the spacing distance between adjacent images/the imaging time, and the electric motor speed is determined according to a set value of the spacing distance between adjacent images. The spacing distance between adjacent images may be greater than the width of field of view of the imaging device. In this case, the images cannot be spliced, but the photographing speed is fast. Certainly, the spacing distance between adjacent images may also be less than the width of field of view of the imaging device. In this case, the adjacent images overlap, and the overlapping images may be spliced into a large image, as shown in FIGS. 23 and 24, FIG. 23 being a schematic diagram before splicing of the overlapping adjacent images, and FIG. 24 being a schematic diagram after splicing.

In some embodiments, the sample carrier holding device 2200 is further configured to move horizontally and vertically so as to enable the sample carrier held on the sample carrier holding device to move under the objective lens 2120 of the imaging device 2100. In this case, preferably, the imaging device 2100 is configured to be fixed, the horizontal drive component 2310 is configured to drive the sample carrier holding device 2200 to enable the sample carrier held on the sample carrier holding device to move horizontally under the imaging device 2100, and the vertical drive component 2320) is configured to drive the sample carrier holding device 2200 to enable the sample carrier held on the sample carrier holding device to move vertically close to or away from the imaging device 2100. In this case, the focusing parameter includes a focusing height, and a representation form of the focusing surface representation function includes a predicted focusing surface. The control device 2400 is configured to control the horizontal drive component to drive the sample carrier holding device to enable the test sample carrier to continuously move horizontally relative to the imaging device, and control the vertical drive component to drive the sample carrier holding device to enable the test sample carrier to move vertically relative to the imaging device, so that the test sample carrier is always on the predicted focusing surface during the continuous horizontal movement.

Figure 25:
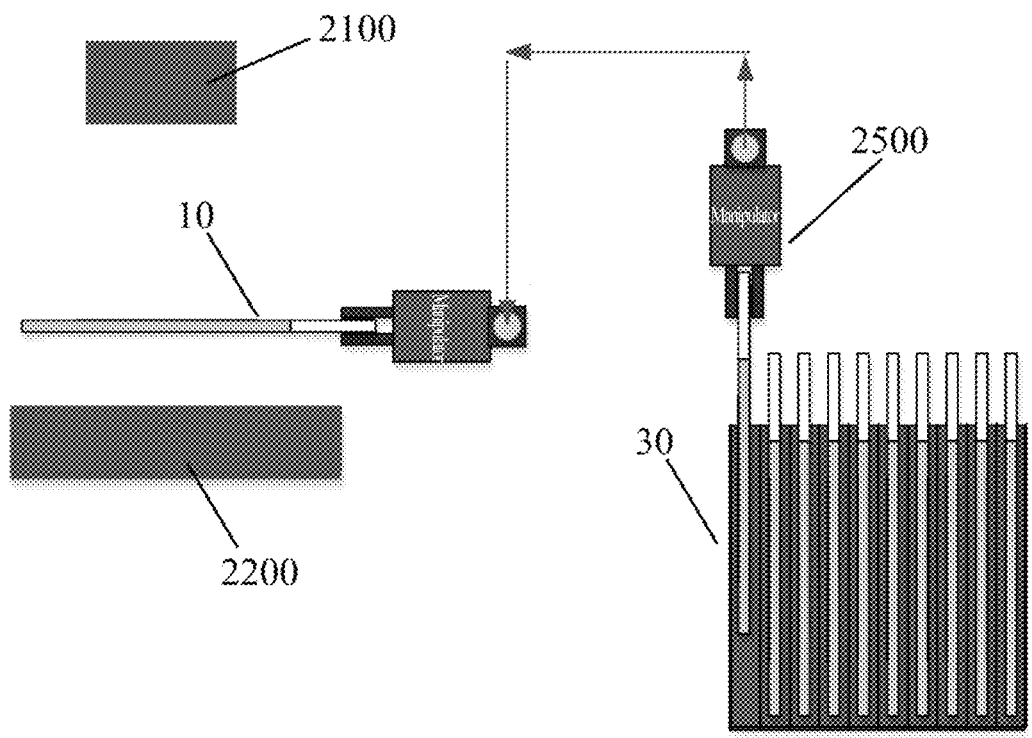
FIGS. 25 and 26 are schematic structural diagrams of another sample image photographing apparatus provided according to an embodiment of the disclosure.
Figure 26:
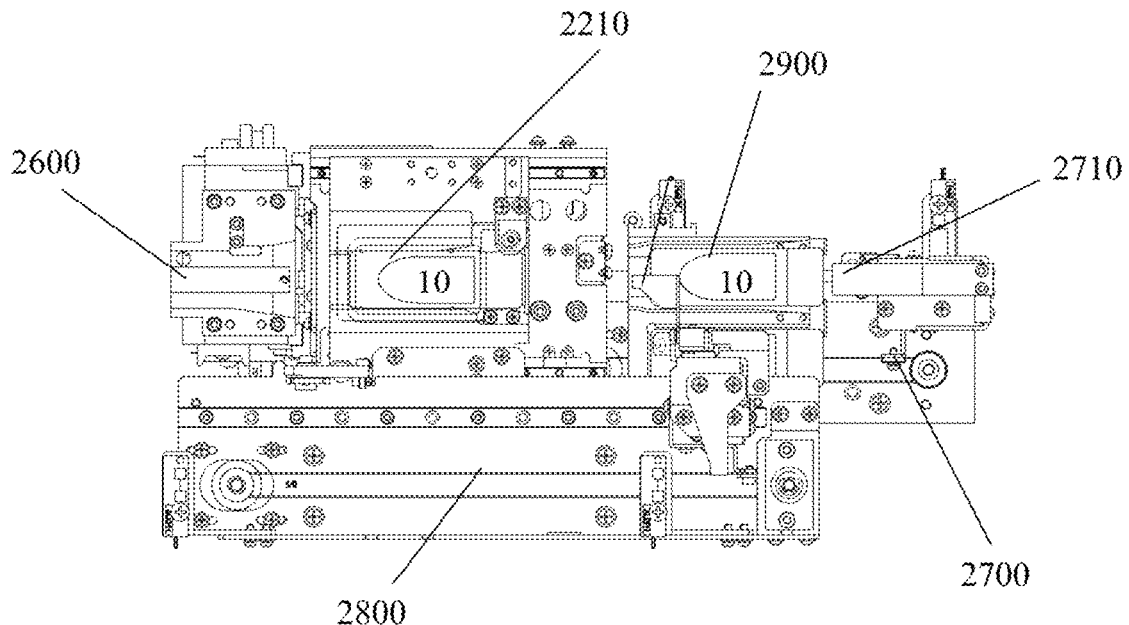

In a specific example, as shown in FIGS. 25 and 26, the sample carrier holding device 2200 is configured as a testing platform 2200 which is provided with a receiving recess 2210 for receiving the test sample carrier 10. The testing platform 2200 is arranged below the imaging device 2100 to enable the imaging device to photograph the sample carrier in the receiving recess 2210 of the testing platform 2200. As shown in FIG. 25, the sample image photographing apparatus further includes a sample carrier transport device 2500, such as a manipulator, and the sample carrier transport device 2500 is configured to transport the test sample carrier 10 from a sample carrier box 30 to the receiving recess 2210 of the testing platform 2200.

As shown in FIG. 26, the sample image photographing apparatus further includes an unloading platform 2600, a loading mechanism 2700, an unloading mechanism 2800, and a loading platform 2900. The loading platform 2900 is configured to temporarily store the test sample carrier 10, and the test sample carrier is placed, for example, by the manipulator 2500 shown in FIG. 24, onto the loading platform in advance for waiting. The loading mechanism 2700 is provided with a push claw 2710 configured such that the test sample carrier placed on the loading platform 2900 is loaded into the receiving recess 2210 of the testing platform 2200, so as to photograph the sample in the test sample carrier by means of the imaging device 2100. The unloading platform 2600 is configured to temporarily store a tested sample carriers, and the unloading mechanism 2800 is configured to unload a tested sample carrier from the receiving recess 2210 of the testing platform 2200 to the unloading platform 2600. When the testing of the sample carrier in the receiving recess 2210 is completed, the unloading mechanism 2800 unloads the sample carrier in the receiving recess 2210 to the unloading platform 2600. In addition, during the unloading, the next test sample carrier on the loading platform 2900 is loaded into the receiving recess 2210 of the testing platform 2200 by means of the loading mechanism 2700. The loading mechanism and the unloading mechanism synchronously operate to implement the synchronous unloading and loading of the tested sample carrier and the next test sample carrier, thereby increasing the photographing speed.

In an alternative embodiment, the sample carrier holding device is configured as a manipulator for gripping a test sample carrier, for example, the manipulator shown in FIG. 25. That is, the testing platform may be omitted, and the manipulator directly enables the gripped test sample carrier to move horizontally and vertically.

In some embodiments, the control device 2400 is configured to control the driving device 2300 and/or the imaging device 2100, so that the area photographed by the imaging device per second is not less than 1 square millimeter, especially not less than 1.3 square millimeters, during the continuous horizontal movement so as to photograph a large-area sample image in a short time.

Figure 27:
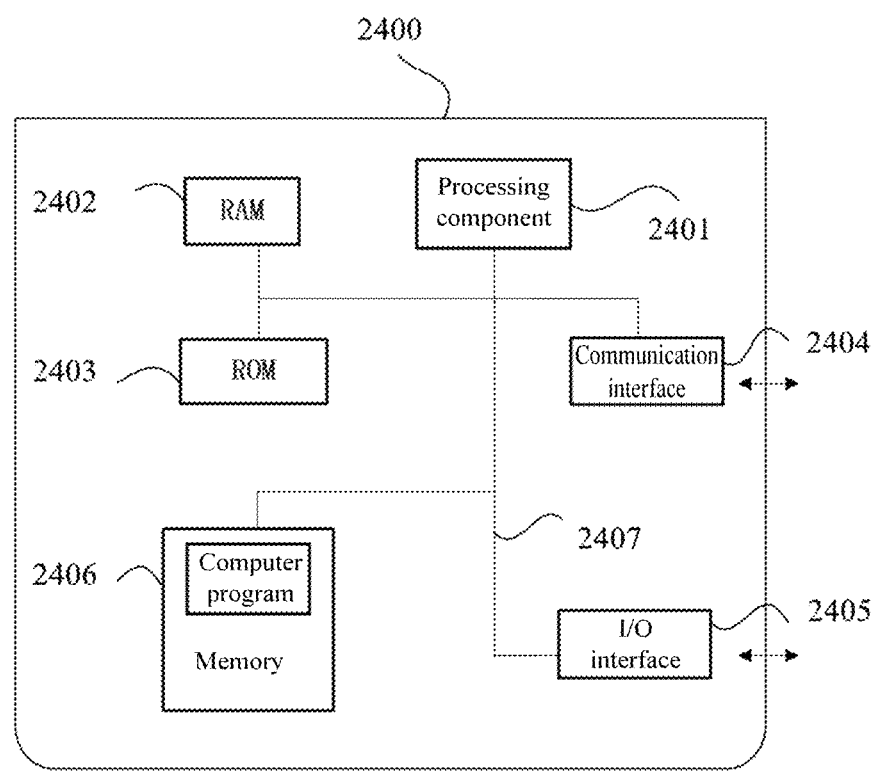
FIG. 27 is a schematic diagram of a control device provided according to an embodiment of the disclosure.

FIG. 27 shows a schematic structural diagram of a control device 2400 provided according to an embodiment of the disclosure. The control device 2400 includes at least a processing component 2401, an RAM 2402, an ROM 2403, a communication interface 2404, a memory 2406, and an I/O interface 2405, where the processing component 2401, the RAM 2402, the ROM 2403, the communication interface 2404, the memory 2406, and the I/O interface 2405 communicate via a bus 2407.

The processing component may be a CPU, a GPU, or another chip having a computing capability. The memory 2406 is loaded with an operating system, various computer programs such as an application program for execution by the processor component 2401, and data required for execution of the computer programs. In addition, during sample photographing, the data that need to be stored locally, such as the horizontal position coordinates and the focusing parameters of the at least three reference points, and/or the focusing surface representation function, the preset photographing path, and sample images, may all be stored in the memory 2406.

The I/O interface 2405 is composed of a serial interface such as USB, IEEE 1394, or RS-232C, a parallel interface such as SCSI, IDE, or IEEE 1284, and an analog signal interface composed of a D/A converter, an A/D converter, etc. An input apparatus composed of a keyboard, a mouse, a touchscreen, or other control buttons is connected to the I/O interface 2405, and a user may directly input data to the control device 2400 by using the input apparatus. In addition, the I/O interface 2405 may be further connected to a display with a display function, for example, a liquid crystal display, a touchscreen, or an LED display screen, and the control device 2400 may output data, such as a sample image, to the display for display.

The communication interface 2404 may be an interface of any communication protocol currently known. The communication interface 2404 communicates with the outside over a network. The control device 2400 may communicate, through the communication interface 2404 and based on a communication protocol, data with any device connected over the network.

For other advantages and features of the sample image photographing apparatus 2000 provided according to the embodiment of the disclosure, reference may be made to the above description of the sample image photographing methods 300 and 1900 provided according to the embodiments of the disclosure and the embodiments thereof, and details are not described herein again.

An embodiment of the disclosure further provides a computer-readable storage medium having stored thereon instructions that, when executed by a processor, cause the processor to implement the above sample image photographing method.

The features or combinations thereof mentioned above in the description, accompanying drawings, and claims can be combined with each other arbitrarily or used separately as long as they are meaningful within the scope of the disclosure and do not contradict each other. The advantages and features described for the sample image photographing method provided with reference to the embodiments of the disclosure are applicable in a corresponding manner to the sample image photographing apparatus and the computer-readable storage medium provided according to the embodiments of the disclosure, and vice versa.

The foregoing description merely relates to the preferred embodiments of the disclosure, and is not intended to limit the scope of patent of the disclosure. All equivalent structural transformations made by using the content of the description and the accompanying drawings of the disclosure from the inventive concept of the disclosure, or the direct/indirect applications of the contents in other related technical fields all fall within the scope of patent protection of the disclosure.

What is claimed is:

1. A sample image photographing method, comprising:
   transporting a test sample carrier by means of a sample carrier transport device to an imaging device comprising a camera and an objective lens;
   obtaining horizontal position coordinates of at least three reference points in a sample area of the test sample carrier by means of a control device;
   moving the test sample carrier horizontally relative to the imaging device by means of a horizontal drive component of a driving device to allow the at least three reference points to separately stop within a field of view of the imaging device, so that the imaging device separately focuses on the at least three reference points;
   determining a focusing surface representation function of the test sample carrier by means of the control device according to the horizontal position coordinates and focusing parameters of the at least three reference points, the focusing surface representation function representing a relationship between horizontal position coordinates and focusing parameter of each point to be photographed in the sample area of the test sample carrier;
   continuously moving the test sample carrier horizontally relative to the imaging device by means of the horizontal drive component of the driving device;
   causing each point to be photographed in the sample area of the test sample carrier to satisfy the focusing surface representation function when said point is within the field of view of the imaging device by means of a vertical drive component of the driving device and/or the imaging device during the continuous horizontal movement; and
   continuously photographing each point to be photographed in the sample area of the test sample carrier by means of the imaging device during the continuous horizontal movement to obtain a sample image.

2. The method of claim 1, wherein the focusing parameter of each point to be photographed comprises a focusing height, and a representation form of the focusing surface representation function comprises a predicted focusing surface; and
   causing each point to be photographed in the sample area of the test sample carrier to satisfy the focusing surface representation function when said point is within the field of view of the imaging device by means of a vertical drive component of the driving device and/or the imaging device during the continuous horizontal movement comprises:
   moving the test sample carrier vertically relative to the imaging device by means of the vertical drive component of the driving device during the continuous horizontal movement, so that each point to be photographed in the sample area of the test sample carrier is on the predicted focusing surface when said point is within the field of view of the imaging device.

3. The method of claim 2, wherein the vertical drive component of the driving device moves the test sample carrier vertically relative to the imaging device while the horizontal drive component of the driving device continuously moves the test sample carrier horizontally relative to the imaging device, so that each point to be photographed in the sample area of the test sample carrier satisfies the focusing surface representation function when said point is within the field of view of the imaging device.

4. The method of claim 2, wherein the horizontal drive component comprises a first electric motor and a second electric motor; and
   continuously moving the test sample carrier horizontally relative to the imaging device by means of the horizontal drive component of the driving device comprises:
   continuously moving the test sample carrier horizontally relative to the imaging device by means of at least one of the first electric motor and the second electric motor.

5. The method of claim 1, wherein the focusing parameter of each point to be photographed comprises an imaging parameter of the imaging device; and
   causing each point to be photographed in the sample area of the test sample carrier to satisfy the focusing surface representation function when said point is within the field of view of the imaging device by means of a vertical drive component of the driving device and/or the imaging device during the continuous horizontal movement comprises:
   adjusting the imaging parameter of the imaging device by means of the control device, so that each point to be photographed in the sample area of the test sample carrier satisfies the focusing surface representation function when said point is within the field of view of the imaging device.

6. The method of claim 1, wherein the horizontal drive component has a driving speed designed such that a distance by which the test sample carrier is moved horizontally relative to the imaging device is not greater than 2 micrometers within an exposure time of the imaging device.

7. The method of claim 1, wherein transporting a test sample carrier by means of a sample carrier transport device to an imaging device comprising a camera and an objective lens comprises: placing the test sample carrier onto a testing platform located below the imaging device by means of the sample carrier transport device; and continuously moving the test sample carrier horizontally relative to the imaging device by means of the horizontal drive component of the driving device comprises: driving the testing platform by means of the horizontal drive component of the driving device to enable the test sample carrier to continuously move horizontally relative to the imaging device.

8. The method of claim 7, wherein the focusing parameter of each point to be photographed comprises a focusing height, and a representation form of the focusing surface representation function comprises a predicted focusing surface; and causing each point to be photographed in the sample area of the test sample carrier to satisfy the focusing surface representation function when said point is within the field of view of the imaging device by means of a vertical drive component of the driving device and/or the imaging device during the continuous horizontal movement comprises:

driving the testing platform by means of the vertical drive component of the driving device during the continuous horizontal movement to enable the test sample carrier to move vertically relative to the imaging device, so that each point to be photographed in the sample area of the test sample carrier satisfies the focusing surface representation function when said point is within the field of view of the imaging device.

9. The method of claim 1, wherein continuously moving the test sample carrier horizontally relative to the imaging device by means of the horizontal drive component of the driving device comprises:

driving the test sample carrier transport device by means of the driving device to enable the test sample carrier to continuously move horizontally relative to the imaging device.

10. The method of claim 2, wherein determining a focusing surface representation function of the test sample carrier according to the horizontal position coordinates and focusing parameters of the at least three reference points comprises:

solving a plane equation a*X+b*Y+c*Z+d=0 according to the horizontal position coordinates and the focusing height of the at least three reference points to obtain a predicted focusing surface, where X and Y represent the horizontal position coordinates, Z represents the focusing height, and a, b, c and d represent coefficients to be solved for the plane equation.

11. The method of claim 1, wherein an area photographed by the imaging device per second is not less than 1 square millimeter during the continuous horizontal movement.

12. The method of claim 1, further comprising:

continuously moving the test sample carrier horizontally relative to the imaging device according to a predetermined photographing path by means of the horizontal drive component of the driving device;

continuously photographing a plurality of sample images of the test sample carrier along the predetermined photographing path by means of the imaging device during the continuous horizontal movement; and determining an area of interest according to the plurality of sample images.

13. The method of claim 12, wherein the at least three reference points are selected from the area of interest, and/or the at least three reference points are not in a same straight line; and/or the at least three reference points are respectively selected from different areas of interest.

14. The method of claim 1, wherein the test sample carrier is a test slide smeared with a blood sample or a body fluid sample or a bone marrow sample.

15. A sample image photographing method, comprising:

transporting a test sample carrier to an imaging device;

determining a focusing surface representation function of a current test sample carrier according to a feature of a sample on the current test sample carrier, the focusing surface representation function representing a relationship between horizontal position coordinates and focusing parameter of each point to be photographed in a sample area of the current test sample carrier;

controlling a horizontal drive component of a driving device to continuously move the current test sample carrier horizontally relative to the imaging device; and causing each point to be photographed in the sample area of the test sample carrier to satisfy the focusing surface representation function when said point is within a field of view of the imaging device during the continuous horizontal movement of the current test sample carrier, so that the imaging device continuously photographs the sample area of the current test sample carrier during the continuous horizontal movement.

16. A sample image photographing apparatus, comprising:

an imaging device, which is provided with a camera and an objective lens and is configured to photograph an image of a sample on a sample carrier;

a sample carrier holding device configured to hold the sample carrier;

a driving device, which is provided with a horizontal drive component configured to enable the sample carrier held by the sample carrier holding device to move horizontally relative to the imaging device and a vertical drive component configured to enable the sample carrier held by the sample carrier holding device to move vertically relative to the imaging device; and a control device, which is in communication connection with the driving device and the imaging device and is configured to:

obtain horizontal position coordinates of at least three reference points in a sample area of a test sample carrier held by the sample carrier holding device;

control the horizontal drive component to move the test sample carrier horizontally relative to the imaging device to allow the at least three reference points to separately stop within a field of view of the objective lens of the imaging device, and control the imaging device to focus on the at least three reference points to obtain focusing parameters of the at least three reference points;

determine a focusing surface representation function of the test sample carrier according to the horizontal position coordinates and the focusing parameters of the at least three reference points, the focusing surface representation function representing a relationship between horizontal position coordinates and focusing parameter of each point to be photographed in the sample area of the test sample carrier;

control the horizontal drive component to continuously move the test sample carrier horizontally relative to the imaging device;

control the vertical drive component and/or the imaging device during the continuous horizontal movement to cause the each point to be photographed in the sample area of the test sample carrier to satisfy the focusing surface representation function when said point is within the field of view of the imaging device; and control the imaging device to continuously photograph each point to be photographed in the sample area of the test sample carrier during the continuous horizontal movement to obtain a sample image.

17. The sample image photographing apparatus of claim 16, wherein the focusing parameter of each point to be photographed comprises a focusing height, and a representation form of the focusing surface representation function comprises a predicted focusing surface; and the control device is configured to control the vertical drive component and/or the imaging device during the continuous horizontal movement to cause the each point to be photographed in the sample area of the test sample carrier to satisfy the focusing surface representation function when said point is within the field of view of the imaging device comprises:

control the vertical drive component during the continuous horizontal movement to move the test sample carrier vertically relative to the imaging device, so that each point to be photographed in the sample area of the test sample carrier is on the predicted focusing surface when said point is within the field of view of the imaging device.

18. The sample image photographing apparatus of claim 16, wherein a driving speed of the horizontal drive component is determined according to a predetermined distance of field of view between two successively photographed adjacent images and/or a photographing frame rate of the imaging device.

19. The sample image photographing apparatus of claim 16, wherein the sample carrier holding device is further configured to be movable horizontally and movable vertically so as to enable the sample carrier held on the sample carrier holding device to move under the objective lens of the imaging device:

the focusing parameter comprises a focusing height, and a representation form of the focusing surface representation function comprises a predicted focusing surface; and the control device is configured to: when the horizontal drive component is controlled to continuously move the test sample carrier horizontally relative to the imaging device, control the horizontal drive component to drive the sample carrier holding device to enable the test sample carrier to continuously move horizontally relative to the imaging device; and when the vertical drive component and/or the imaging device is controlled during the continuous horizontal movement to cause the each point to be photographed in the sample area of the test sample carrier to satisfy the focusing surface representation function when being within the field of view of the imaging device, control the vertical drive component to drive the sample carrier holding device to enable the test sample carrier to move vertically relative to the imaging device, so that the test sample carrier is on the predicted focusing surface during the continuous horizontal movement.

20. The sample image photographing apparatus of claim 16, wherein the control device comprises a storage device configured to store the horizontal position coordinates of the at least three reference points and/or the focusing surface representation function.

* * * * *